United States Patent
Abraham-Fuchs et al.

(10) Patent No.: US 7,881,949 B2
(45) Date of Patent: Feb. 1, 2011

(54) METHOD FOR AUTOMATED RECORDING OF PATIENT ACTIONS

(75) Inventors: Klaus Abraham-Fuchs, Erlangen (DE); Eva Rumpel, Erlangen (DE); Daniel Tietze, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 2451 days.

(21) Appl. No.: 10/395,246

(22) Filed: Mar. 25, 2003

(65) Prior Publication Data

US 2003/0229518 A1 Dec. 11, 2003

(30) Foreign Application Priority Data

Mar. 25, 2002 (DE) .................... 10 213 283

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. .................... 705/3; 705/2; 705/4
(58) Field of Classification Search .............. 705/1, 705/2, 3, 4
See application file for complete search history.

(56) References Cited

U.S. PATENT DOCUMENTS

| | | | | |
|---|---|---|---|---|
| 5,576,952 | A * | 11/1996 | Stutman et al. | 600/300 |
| 5,666,490 | A * | 9/1997 | Gillings et al. | 709/238 |
| 5,991,731 | A * | 11/1999 | Colon et al. | 705/3 |
| 5,997,476 | A * | 12/1999 | Brown | 600/300 |
| 6,033,365 | A | 3/2000 | Von Zitzewitz | |
| 6,141,609 | A * | 10/2000 | Herdeg et al. | 701/35 |
| 6,490,443 | B1 * | 12/2002 | Freeny, Jr. | 455/406 |
| 6,539,101 | B1 * | 3/2003 | Black | 382/124 |
| 6,579,231 | B1 * | 6/2003 | Phipps | 600/300 |
| 6,820,235 | B1 * | 11/2004 | Bleicher et al. | 715/236 |
| 2001/0056358 | A1 | 12/2001 | Dulong et al. | |
| 2002/0041175 | A1 * | 4/2002 | Lauper et al. | 320/106 |

FOREIGN PATENT DOCUMENTS

WO 0195793 12/2001

* cited by examiner

*Primary Examiner*—Gerald J. O'Connor
*Assistant Examiner*—Amber Altschul

(57) ABSTRACT

A method is for automated recording of patient actions, for example in the course of telemedical care, in the course of clinical studies for the merit of a form of therapy or for trialing the effectiveness of drugs. The medical equipment or devices used in this context are provided with recording devices for identifying the patient so that the data obtained during use of the equipment or accessories can automatically be attributed to the patient in question.

32 Claims, 1 Drawing Sheet

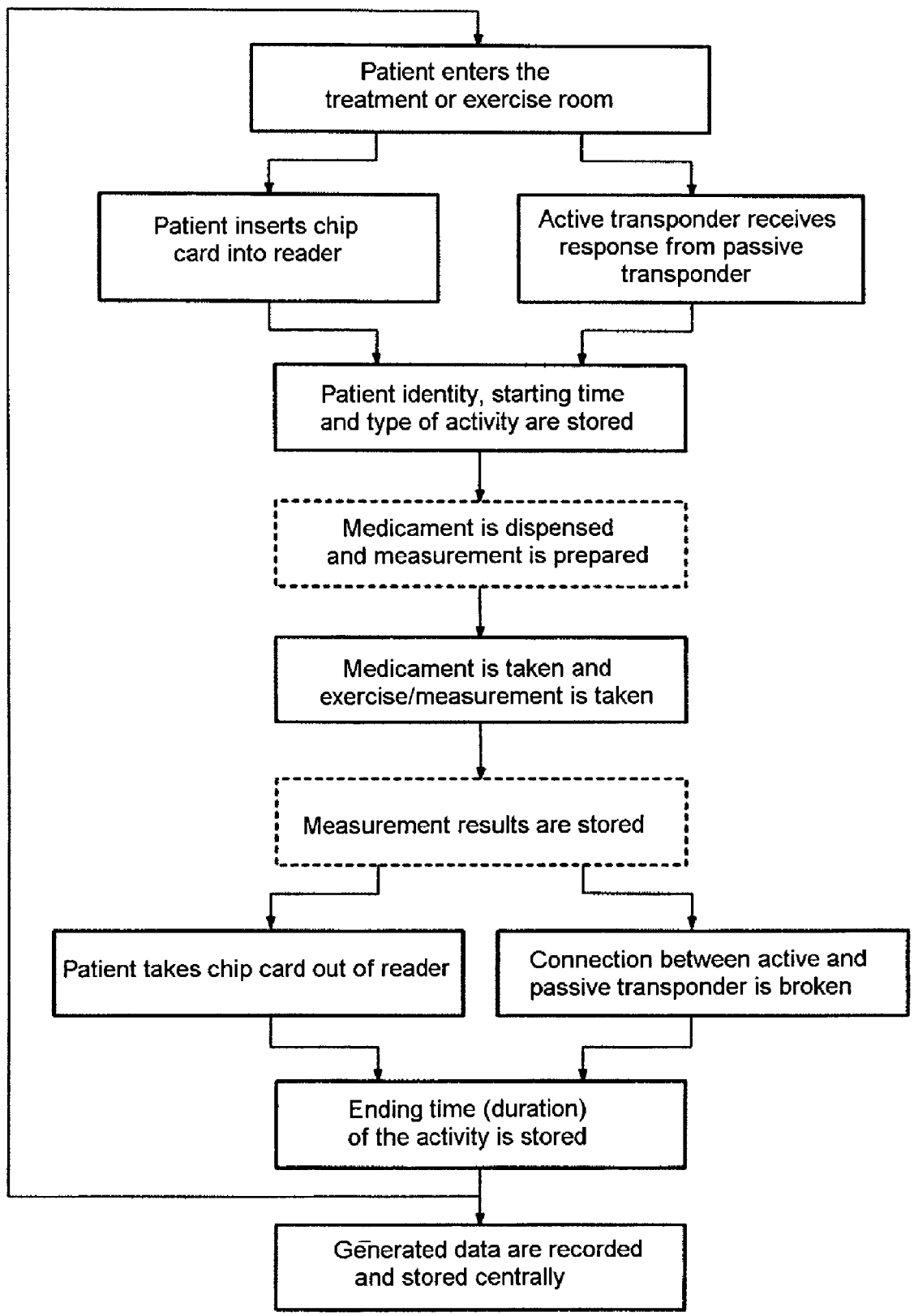

METHOD FOR AUTOMATED RECORDING OF PATIENT ACTIONS

The present application hereby claims priority under 35 U.S.C. §119 on German patent application number DE 10213283.6 filed Mar. 25, 2002, the entire contents of which are hereby incorporated herein by reference.

FIELD OF THE INVENTION

The invention generally relates to a method for automated recording of patient actions, for example in the course of telemedical care or in the course of clinical studies for the merit of a form of therapy or for trialing the effectiveness of drugs.

BACKGROUND OF THE INVENTION

A great problem in patient therapy is that it is often not possible to check how precisely the patient is sticking to the physician's prescriptions ("compliance"), i.e. whether and when he is taking his medicaments or, by way of example, is determining his blood sugar or how often and for how long he performs the exercises which he has been instructed to do. This information is extremely important, however, if it is necessary to assess the merit of a form of therapy or, by way of example, the effectiveness of a new medicament. Thus, when introducing new medicaments, for example, clinical studies are prescribed which prove a 10 to 20% better action as compared with an existing preparation or a placebo. This requires—on account of the high variability of the measured values—very large numbers of participants. The pharmaceutical industry assumes that 30 to 40% of the variability of the measured values can be attributed to a lack of standardization of boundary conditions: medicaments are not taken, or are not taken punctually, measured values are collected at different times and/or in a wide variety of ways etc. A similar situation applies to studies for assessing therapy results ("outcome analysis") if it is not known how precisely the individual patients have stuck to their instructions. Finally, a comparable problem also arises with patients who have been given novel forms of telemedical care.

To date, the lack of standardization has been compensated for by increasing the number of subjects under test, which is time-consuming and cost-intensive. Such studies are still predominantly paper-based even today, i.e. questionnaires and/or survey sheets are filled in, collected and finally evaluated centrally. The correctness of the details can usually be checked—if at all—only in the form of plausibility checks.

The problems mentioned above have also not been able to be solved by a piece of equipment for recording values relating to state of health, as described in DE 196 14 255 C1. This merely involves the patient carrying around a mobile piece of equipment into which he enters respective data about medicaments taken, state of health etc. Whether a patient has actually been to and used a particular piece of therapy equipment, and if so, for what length of time, or whether or not he has taken the tablets, can be assessed with this test equipment only in the case of patients who are very careful, however. If the patient takes the tablets without using his equipment, this cannot be detected. A crucial factor, however, is that this merely involves a patient entering his data into a piece of recording equipment which he has. When patient actions are recorded automatically, however, a large amount of equipment and devices can be used which are not associated with the patient personally and which therefore also have no knowledge at all about who is using them.

The same also applies to an equipment system intended to be used in DE 100 54 960 A1 for examining the state of a patient and his readiness to cooperate and/or to prepare for therapy. This document merely involves access authorization for assessing the patient file, which requires user identification. In this arrangement, the equipment being used knows the particular person using it, which is not currently the case with real examinations of compliance.

SUMMARY OF THE INVENTION

An embodiment of the invention is therefore based on an object of providing a method for automated recording of patient actions. Preferably, it relates to one which has a much higher level of standardization and largely prevents widespread cheating in data collection both by the patient and by the clinical personnel in the course of clinical studies.

An embodiment of the invention achieves this object by providing that the medical equipment or devices used in this context be provided with recording devices for identifying the patient so that the data obtained during use of the equipment or accessories can automatically be attributed to the patient in question. Such identification equipment can be, by way of example, chip cards, transponders or the like, with the recording devices then being suitable counterparts, e.g. chip card reader, transponder counterpart or the like.

The identification apparatus used can also be an apparatus for identifying biometric features, such as fingerprints.

An inventive embodiment allows automatic recording of which patient has produced which measured value, for example, which accessory he has used or, if appropriate, which treatment room he has visited, and at the same time recording of the time at which this action was performed.

This type of automatic recording of which patient has produced which measured value, with the equipment previously not having known the patient at all, also constitutes the crucial difference from the arrangements based on the prior art documents cited at the outset. According to an embodiment of the invention, the equipment or the respective device does not know the patient, and there is thus no comparison of the partner's identification with stored data, but rather the recording devices for identification are used to provide the equipment values produced with a user address which can then be taken as a basis for evaluating the equipment's measured values in a central station. In this case, within the context of the invention, the term "data obtained" is to be understood not just to mean a measured value produced by a piece of equipment but also, by way of example, the fact that a patient has entered a particular room or has used a particular piece of equipment—regardless of how. These are also relevant data in connection with clinical studies or examinations of compliance.

The data recorded in this manner are provided not only with the identity of the patient but also preferably with a time stamp and can optionally be stored with the patient, e.g. on his chip card, at the individual network points, e.g. in a computer connected to the chip card reader or to the transponder point, or finally also centrally, e.g. on a computer networked to the individual collection points. This firstly prevents copying errors (e.g. from an instrument's display to a measurement log or from the measurement log to the survey sheet) and also (consciously or unconsciously) incorrect details from the person involved regarding time, duration and type of the actions performed.

The data collected in this manner allow, by way of example, automatic checking of whether a patient is satisfying the inclusion criteria for evaluating the study or whether his data should be disregarded, e.g. on account of the medicaments being taken too irregularly. This reduces the variability of the results and improves the significance of the analysis. It is also conceivable for the number of participants to be reduced, because the reduced variability allows significant statements to be made more easily, i.e. with fewer random samples. The system described is also particularly suitable for monitoring the compliance of patients who have been given novel forms of telemedical care.

In another embodiment of the invention, the stored data are compared against nominal specified values stored in the recording apparatus, in the connected computer or in the networked central computer, and the patient action is identified as being in line with the nominal specified values or not in line with the nominal specified values, in which case, preferably, only actions identified as being in line with the nominal specified values are transferred to the database for the purpose of evaluating a clinical study. Within the context of telemedical care, all actions which are not in line with the nominal specified values can be sent via the connected data network with a warning to the responsible medical carer.

BRIEF DESCRIPTION OF THE DRAWINGS

Other advantages, features and details of the invention can be found in the description below of an exemplary embodiment and with reference to the drawing, which shows a flowchart for an inventive automated recording system.

DETAILED DESCRIPTION OF THE PREFERRED EMBODIMENTS

As soon as the patient enters the treatment or exercise room, either he inserts his identification equipment, for example a chip card, into a corresponding reader or else an active transponder in the room or on the examination equipment or exercise equipment receives a response from the passive transponder in the patient's identification equipment. The patient identity, the starting time and the type of activity are stored. If appropriate, the medicament to be taken is dispensed and a measurement is prepared. When the medicament has been taken and the exercise or measurement has been taken, the measurement results are stored. On leaving the treatment or exercise room, either the patient takes his chip card out of the reader or else the connection between active and passive transponder is broken, and in both cases this is stored as the ending time (duration) for the activity. Following local recording and storage of the data produced, these data are, if appropriate, transmitted via a data network to a central database and are stored centrally therein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for recording of patient actions for tracking patient progress of participants in the course of clinical studies suitable for trialing the effectiveness of drugs, comprising:
providing medical equipment able to obtain patient medical data from the patient at a treatment facility with a recording device for acquiring patient identification information from an electronic wirelessly communicating patient identification device carried by the patient, wherein said medical equipment is unaware of patient identification information prior to acquisition of said identification information;
acquiring, from said patient identification device, data for identifying a patient and a patient location address;
automatically associating data obtained during use of the medical equipment in a clinical study with the data identifying the patient and patient location address; and
automatically communicating said associated data via a communications network to an evaluation station for monitoring progress of the participants in the clinical study; and
storing said associated data in a storage device.

2. The method as claimed in claim 1, wherein the recording device for identifying the patient includes at least one of a chip card reader and a transponder and said patient identification device is individually assigned to a respective patient and is at least one of a counterpart chip card and a counterpart of the transponder.

3. The method as claimed in claim 2,
wherein the storage device is located in at least one of the recording device for patient identification, in therapy equipment, in data collection equipment, in a technical accessory and in an individual chip card.

4. The method as claimed in claim 2,
wherein the storage device is a data collection point residing in a computer connected to the recording device.

5. The method as claimed in claim 2, further comprising using an apparatus residing in a recording device in at least one of the medical equipment or device and the patient identification equipment for determining at least one of treatment facility location and patient location.

6. The method as claimed in claim 1,
wherein said storage device is at least one of in the recording device for patient identification, in therapy equipment, in data collection equipment in a technical accessory and in an individual chip card.

7. The method as claimed in claim 6, wherein the data obtained and associated with the patient are stored in a computer connected to the recording device.

8. The method as claimed in claim 1,
wherein said storage device is a data collection point located at the treatment facility.

9. The method as claimed in claim 1,
wherein said evaluation station is a central evaluation station remotely located from the treatment facility and said storage device is a central computer networked to a plurality of different data collection points at a plurality of different treatment facilities.

10. The method as claimed in claim 9, further comprising:
comparing the stored data are against nominal specified values; and
identifying the patient action as being in line with the nominal specified values or not in line with the nominal specified values.

11. The method as claimed in claim 1, wherein said patient address location data includes data representing at least one of a place of collection, a location of a treatment facility, a room within a respective treatment facility, type of collection equipment used to obtain patient data, a start time indicating collection of data has begun and an end time indicating collection of data has ended.

12. The method as claimed in claim 1, wherein each patient participant is identified by a predetermined biometric feature, and said recording device further records a biometric feature of said patient in response to clinical study information data identifying the biometric feature and stored on said patient identification device.

13. The method as claimed in claim 12, wherein the recording device for identifying the patient records a fingerprint of the patient.

14. The method as claimed in claim 12,
wherein said storage device is in at least one of the recording device for patient identification, in therapy equipment, in data collection equipment, in a technical accessory and an individual chip card.

15. The method as claimed in claim 12,
wherein the storage device is a data collection point residing in a computer connected to the recording device.

16. The method as claimed in claim 12, wherein said patient address location data includes data representing at least one of a place of collection, a location of a treatment facility, a room within a respective treatment facility, type of collection equipment used to obtain patient data, a start time indicating collection of data has begun and an end time indicating collection of data has ended.

17. The method as claimed in claim 16, further comprising obtaining patient address location information using a GPS system.

18. The method as claimed in claim 1, further comprising:
comparing the stored data are against nominal specified values; and
identifying the patient action as being in line with the nominal specified values or not in line with the nominal specified values.

19. The method as claimed in claim 18, further comprising:
communicating only data representing actions identified as being in line with the nominal specified values to a database for the purpose of evaluating a clinical study.

20. The method as claimed in claim 19, wherein within the context of telemedical care, actions which are not in line with the nominal specified values, causing a warning to be sent to the responsible medical caregiver via the connected data network.

21. The method as claimed in claim 18, wherein in response to determining actions which are not in line with the nominal specified values, automatically causing a warning to be sent to the responsible medical caregiver via a connected data network.

22. The method of claim 1, wherein said automatic associating and communicating of patient data ensures reliability of said recorded data by preventing errors associated with manual transfer of data from the medical equipment.

23. The method as claimed in claim 1, wherein said patient address location data includes data representing at least one of a place of collection, a location of a treatment facility, a room within a respective treatment facility, type of collection equipment used to obtain patient data, a start time indicating collection of data has begun and an end time indicating collection of data has ended.

24. The method as claimed in claim 1, further comprising obtaining patient address location information using a GPS system.

25. A method for recording of patient actions for tracking patient progress of participants in the course of clinical studies suitable for trialing the effectiveness of drugs, comprising:
providing medical equipment able to obtain patient medical data from the patient at a treatment facility with a biometric recording device for acquiring patient identification information by recording a predetermined biometric feature of the patient, wherein said medical equipment is unaware of patient identification information prior to acquisition of said biometric identification information;
acquiring, from said recorded biometric feature, data identifying a patient and a patient location address;
automatically associating data obtained during use of the medical equipment in a clinical study with the data identifying the patient and patient location address;
automatically communicating said associated data via a communications network to an evaluation station for monitoring progress of the participants in the clinical study; and
storing said associated data in a storage device.

26. The method as claimed in claim 25, wherein said predetermined biometric feature is a patient fingerprint and the recording device for identifying the patient records a fingerprint of the patient.

27. The method as claimed in claim 25, further comprising:
comparing the stored data are against nominal specified values; and
identifying the patient action as being in line with the nominal specified values or not in line with the nominal specified values.

28. The method as claimed in claim 27, further comprising:
communicating only data representing actions identified as being in line with the nominal specified values to a database for the purpose of evaluating a clinical study.

29. The method as claimed in claim 25, wherein in response to determining actions which are not in line with the nominal specified values, automatically causing a warning to be sent to the responsible medical caregiver via a connected data network.

30. The method as claimed in claim 25,
wherein said storage device is in at least one of the recording device for patient identification, in therapy equipment, in data collection equipment, in a technical accessory and in an individual chip card.

31. The method as claimed in claim 25,
wherein the storage device is a data collection point residing in a computer connected to the recording device.

32. The method as claimed in claim 25, wherein said patient address location data includes data representing at least one of a place of collection, a location of a treatment facility, a room within a respective treatment facility, type of collection equipment used to obtain patient data, a start time indicating collection of data has begun and an end time indicating collection of data has ended.

* * * * *